United States Patent [19]
Demachi et al.

[11] Patent Number: 5,390,552
[45] Date of Patent: Feb. 21, 1995

[54] VALVE FOR SAMPLING A LIQUID SPECIMEN

[75] Inventors: Takashi Demachi, Kobe; Toshiaki Kuroda, Takasagoshi, both of Japan

[73] Assignee: Toa Medical Electronics Co., Ltd., Kobe, Japan

[21] Appl. No.: 969,574

[22] Filed: Oct. 30, 1992

[30] Foreign Application Priority Data

Nov. 20, 1991 [JP] Japan .................. 3-331283

[51] Int. Cl.⁶ .............................................. G01N 1/10
[52] U.S. Cl. ............................................... 73/863.730
[58] Field of Search ........... 73/863.73, 863.71, 863.72, 73/864.11, 864.12; 422/103

[56] References Cited
U.S. PATENT DOCUMENTS

| | | | |
|---|---|---|---|
| 3,885,439 | 5/1975 | Stone | 73/863.73 |
| 3,964,513 | 6/1976 | Molner | 73/863.73 X |
| 4,152,391 | 5/1979 | Cabrera | 422/103 |
| 4,445,391 | 5/1984 | Cabrera | 422/103 X |
| 4,506,558 | 3/1985 | Bakalyar | 73/863.72 |
| 4,507,977 | 4/1985 | Cabrera | 422/103 X |
| 4,625,569 | 12/1986 | Toei et al. | 73/863.72 |
| 4,702,889 | 10/1987 | Cabrera et al. | 73/863.73 X |
| 4,726,237 | 2/1988 | Yung | 73/863.73 X |
| 4,726,932 | 2/1988 | Feier et al. | 73/863.73 X |
| 4,822,569 | 4/1989 | Pellegrino | 73/863.73 X |
| 4,896,546 | 1/1990 | Cabrera et al. | 73/863.73 |
| 4,948,565 | 8/1990 | Bemis et al. | 73/863.73 X |
| 4,957,008 | 9/1990 | Proni et al. | 73/863.73 X |
| 5,207,109 | 5/1993 | Olsen | 73/863.73 |

*Primary Examiner*—Hezron E. Williams
*Assistant Examiner*—Daniel S. Larkin
*Attorney, Agent, or Firm*—Jones, Tullar & Cooper

[57] ABSTRACT

A sampling valve comprises two fixed elements, and a movable element held between these fixed elements, in which a flow-in passage (Q) is provided at one fixed element so as to communicate with at least one of the metering passages (P1) , . . . . Plural flow-out passages (R1), (R2), . . . are provided at the other or one fixed element so as to communicate with different metering passages individually. Relay passages (S1), . . . are also provided at the one or other fixed element so as to mutually connect the metering passages (P1), (P2), . . . in specified combinations. In such a construction, plural sampling routes are formed in the sampling valve. In the sampling valve for aspirating and pushing liquid specimens such as blood in cylindrical shape and removing it quantitatively, only the portion necessary for measurement may be selected and sampled.

4 Claims, 7 Drawing Sheets

VALVE FOR SAMPLING A LIQUID SPECIMEN

BACKGROUND OF THE INVENTION

The present invention relates to a sampling valve for aspirating and pushing a liquid specimen such as blood in cylindrical shape, and sampling quantitatively, and more particularly to a sampling valve for sampling by selecting only a portion of the sample necessary for measurement.

An apparatus for counting blood corpuscles such as erythrocytes, an apparatus for classifying leukocytes, and an apparatus for counting reticulocytes are well known. An apparatus which combines these plural functions into one (multifunctional apparatus) is also known. The multifunctional apparatus is capable of obtaining measuring results of multiple items by one sampling operation. Depending on the specimen, however, unnecessary items are also measured, and the samples and reagents are spent wastefully.

To eliminate such waste, a function for sampling and taking into the apparatus to analyze (discrete test function) only a necessary sample for each specimen is required. For example, in the field of biochemical examination, the sampling method includes aspirating a necessary amount of sample from a pipette, and discharging the sample into a reaction vessel. This method requires a simple structure, but precision is poor. In particular, it is a problem when handling a highly viscous sample such as blood. Accordingly, in the blood cell counting apparatus, the specimen is sampled by aspirating and pushing the specimen in cylindrical shape by means of a sampling valve, and quantitative removal.

Figure 1:
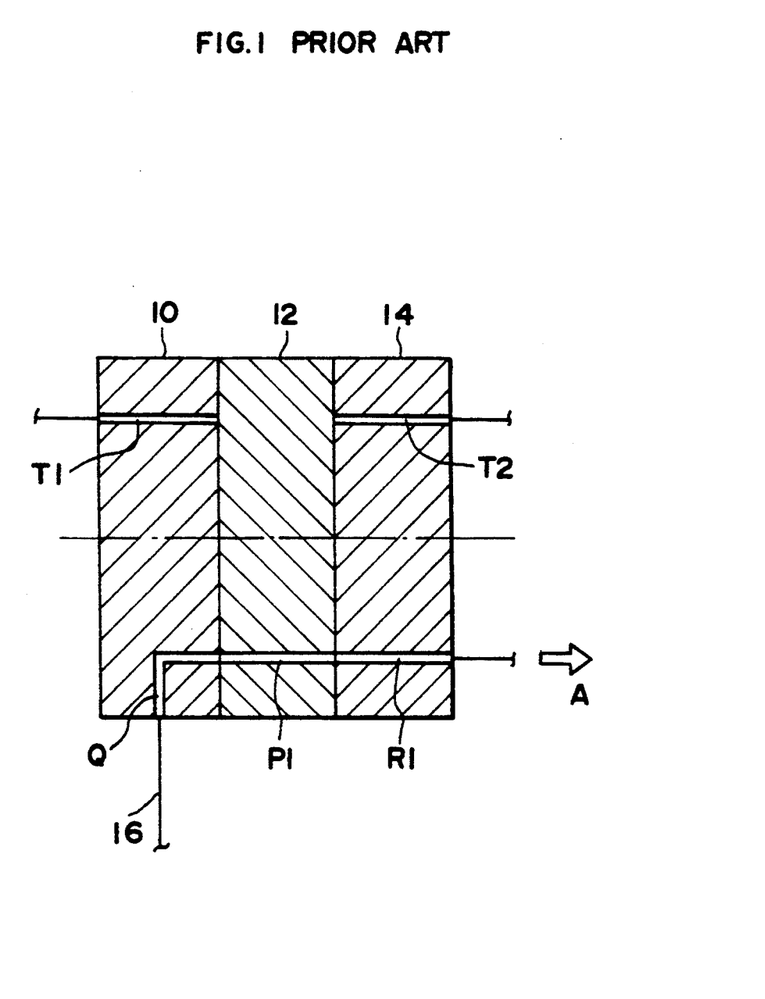
FIG. 1 is a sectional view showing a first stale of filling a metering passage with sample in a known, generally conventional sampling valve.
Figure 2:
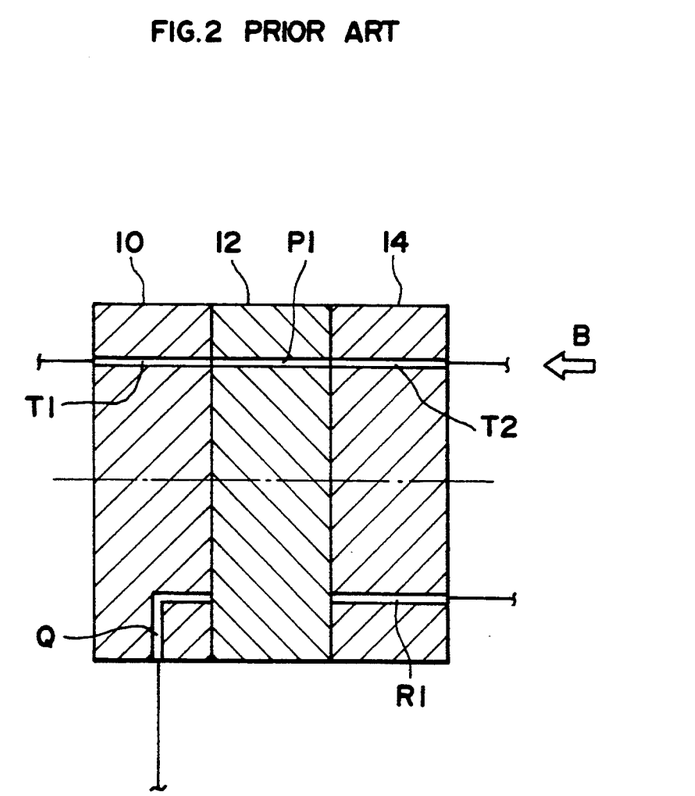
FIG. 2 is a sectional view showing a second state of pushing out and transferring the sample in the generally conventional sampling valve.

Referring now to FIG. 1 and FIG. 2, the structure and operation of a general sampling valve are briefly described below. Usually, a sampling valve consists of two fixed elements 10, 14 and a movable element 12 enclosed by the fixed elements 10, 14. FIG. 1 and FIG. 2 show two states of the sampling valve. In FIG. 1, the specimen flows in the direction of arrow A, that is, from a pipette 16 to a flow-in passage Q, metering (measuring quantity) passage P1, and flow-out passage R1, and fills up the metering passage P1 of the movable element 12 (which is called the first state). As the movable element 12 moves from the first state, it comes to the state in FIG. 2 (which is called a second state), and the specimen in the metering passage P1 in the first state is pushed out, and is transferred outside the sampling valve, together with a liquid such as a diluent in the direction of arrow B from the passage T2 to the passage T1.

In the apparatus for sampling a specimen by means of a sampling valve, there has been a keen desire for a sampling valve applicable to a discrete test in order to realize such discrete test as mentioned above (for sampling only a necessary portion in each specimen and analyzing).

OBJECT AND SUMMARY OF THE INVENTION

It is therefore a primary object of the present invention to provide a sampling valve applicable to a discrete test capable of selecting only a necessary portion of sample required for measurement and quantitative sampling.

To achieve the above object, the sampling valve of the present invention comprises two fixed elements in a stationary state, and a movable element held and moving between these fixed elements, having plural sample metering passages disposed in the movable element, and moving the movable element while contacting the surface of the fixed elements so as to have a first state for filling the metering passages with sample and a second state for pushing out the filling sample in cylindrical shape and transferring it outside of the sampling valve, which further comprises a flow-in passage disposed in one fixed element for communicating with at least one metering passage in the first state, plural flow-out passages disposed in other or one fixed element so as to communicate with mutually different metering passages, and relay passages disposed in one or other fixed element for mutually connecting the metering passages in specified combination, wherein at least one relay passage is connected with any one of the flow-in passages, flow-out passages, and other relay passages to form plural sampling routes in the sampling valve, thereby sampling the specimen by selecting a specific metering passage.

In this sampling valve, the passages are disposed so that plural metering passages may be connected in series, or passages are disposed so that plural metering passages may be connected in parallel, or passages are disposed so that plural metering passages may be connected in series and parallel combination.

Meanwhile, the flow-in passage is the passage serving as the inlet for leading the specimen into the sampling valve from outside as the time of aspirating the specimen, and the flow-out passage is the passage serving as the outlet for sending out the specimen once led into the sampling valve to the outside.

When using the sampling valve of the present invention, a pipette is connected to the flow-in passage, and suction (aspiration) means is connected to the flow-out passages. In the first state, the pipette is dipped in the sample liquid, and the suction means is operated. At this time, an aspiration pressure is applied by selecting only a certain flow-out passage by, for example, a change-over valve. This aspiration pressure reaches the flow-in passage and pipette through the specified passage within the sampling valve, and the sample is aspirated from the pipette. The sample, depending on the connection state of the passages in the sampling valve, flows through a certain sampling route, and the metering passage in that sampling route is filled up. In other sampling routes, sample does not flow and is not determined quantitatively. When an aspiration pressure is applied to the other flow-out passage, the other metering passage is filled with sample.

In this way, by applying an aspiration pressure by selecting one of the plural flow-out passages, a different sampling route is selected, that is, a metering passage is selected, so that the sample may be taken out. The passages in the sampling valve may be meanwhile composed in an optimum connection state depending on the purpose.

When the aspiration of the sample is over, the sampling valve falls in the second state, and the sample is pushed out in cylindrical shape, and is transferred to the measuring part disposed outside of the sampling valve. Successively, the sampling valve returns to the first state, and each passage is cleaned with a cleaning liquid (syringe liquid) from a cleaning liquid tank.

DETAILED DESCRIPTION OF THE PREFERRED EMBODIMENTS

Referring now to the drawings, some of the preferred embodiments of the present invention are described in detail below.

The sampling valve of the present invention, as explained by reference to FIG. 3 to FIG. 7, comprises two fixed elements 10, 14 in a stationary state, and a movable element 12 held and moving between these fixed elements, having plural sample metering passages P1, P2, . . . disposed in the movable element 12, and moving the movable element 12 while contacting with the surface of the fixed elements 10, 14 so as to have a first state of filling the metering passages with sample and a second state of pushing out the filling sample in cylindrical shape and transferring it outside of the sampling valve, which further comprises

- a flow-in passage Q disposed in one fixed element for communicating with at least one metering passage in the first state,
- plural flow-out passages R1, R2, . . . disposed in the other or one fixed element so as to communicate with mutually different metering passages, and
- relay passages S1, . . . disposed in one or the other fixed element for mutually connecting the metering passages P1, P2, . . . in specified combination, wherein
- at least one relay passage is connected with any one of the flow-in passage Q, flow-out passages R1, R2, . . . , and the other relay passage to form plural sampling routes in the sampling valve, thereby sampling the specimen by selecting a specific metering passage.

When using the sampling valve of the present invention, a pipette 16 is connected to the flow-in passage Q, and suction (aspiration) means 18 is connected to flow-out passages R1, R2, . . . . In the first state, the pipette 16 is dipped in the sample liquid, and the suction means 18 is operated. At this time, an aspiration pressure is applied by selecting only a certain flow-out passage by, for example, a changeover valve. This aspiration pressure reaches the flow-in passage Q and pipette 16 through the specified passage within the sampling valve, and the sample is aspirated from the pipette 16. The sample, depending on the connection state of the passages in the sampling valve, flows through a certain sampling route, and the metering passage in that sampling route is filled up. In other sampling routes, the sample does not flow and is not measured quantitatively. When an aspiration pressure is applied to other flow-out passages, the other metering passage is filled with sample.

When the aspiration of the sample is over, the sampling valve falls into the second state, the sample is pushed out in cylindrical shape, and is transferred to the measuring part disposed outside of the sampling valve. Successively, the sampling valve returns to the first state, and each passage is cleaned with a cleaning liquid (syringe liquid) from a cleaning liquid tank 20.

Figure 3:
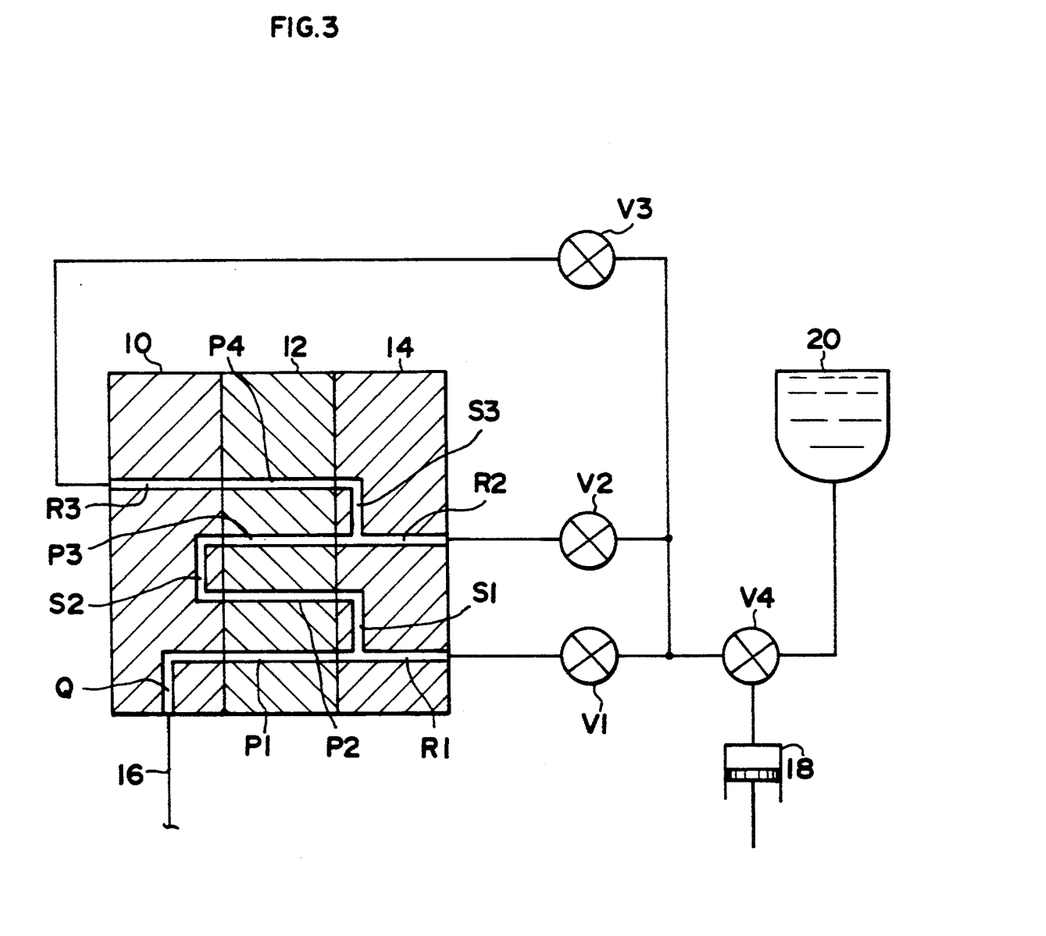
FIG. 3 is a sectional view showing an embodiment of a sampling valve of the present invention.

FIG. 3 shows a case in which four metering passages are disposed, with metering passages P1, P2, P3, P4 being connected in series, and three sampling routes mutually overlapped in part. More specifically, symbol Q denotes a flow-in passage, S1, S2, S3 are relay passages, R1, R2, R3 are flow-out passages, and the relay passage S1 connects the flow-out passage R1 with the metering passage P2, and the relay passage S3 connects the flow-out passage R2 with the metering passage P4.

When a valve V1 is open, and valves V2, V3 are closed, by changing over a three-way valve V4 so that aspiration means 18 and valve V1 communicate with each other, sample flows from pipette 16 through passages Q, P1, R1 (the first sampling route), and is measured quantitatively in the passage P1.

When the valve V2 is open, and the valves V1, V3 are closed, sample flows from the pipette 16 through passages Q, P1, S1, P2, S2, P3, R2 (the second sampling route), and is measured quantitatively in the passages P1, P2, P3.

When the valve V3 is open, and the valves V1, V2 are closed, sample flows from the pipette 16 through passages Q, P1, S1, P2, S2, P3, S3, P4, R3 (the third sampling route), and is measured quantitatively in the passages P1, P2, P3, P4.

Figure 4:
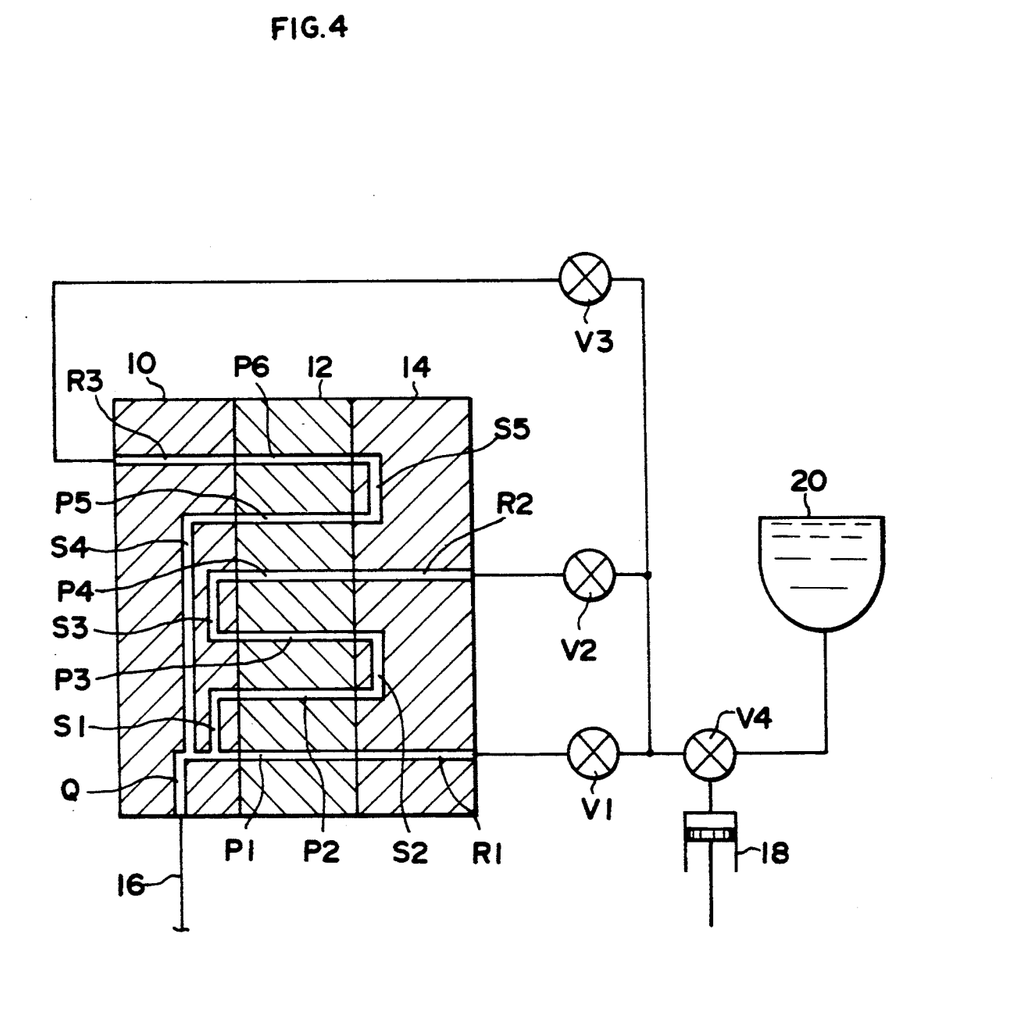
FIG. 4 is a sectional view showing another embodiment of a sampling valve of the present invention.

FIG. 4 shows a case in which six metering passages are disposed, and these metering passages P1, P2, P3, P4, P5, P6 are connected in parallel (partly in series, however, in this embodiment), and three sampling routes are in parallel relation. More specifically, symbol Q denotes a flow-in passage, S1, S2, S3, S4, S5 are relay passages, R1, R2, R3 are flow-out passages, and the relay passages S1, S4 are connected with the flow-in passage Q and metering passages P2 and P5, respectively. Meanwhile, the relay passage S1 may be connected with the flow-in passage Q, and the passage S4 with passage S1.

When the valve V1 is open, and valves V2, V3 are closed, by changing over a three-way valve V4 so that aspiration means 18 and valve V1 may communicate with each other, sample flows from a pipette 16 through passages Q, P1, R1 (the first sampling route), and is measured quantitatively in the passage P1.

When the valve V2 is open, and the valves V1, V3 are closed, sample flows from the pipette 16 through passages Q, S1, P2, S2, P3, S3, P4, R2 (the second sampling route), and is measured quantitatively in the passages P2, P3, P4.

When the valve V3 is open, and the valves V1, V2 are closed, sample flows from the pipette 16 through passages Q, S4, P5, S5, P6, R3 (the third sampling route), and is measured quantitatively in the passages P5, P6.

Figure 5:
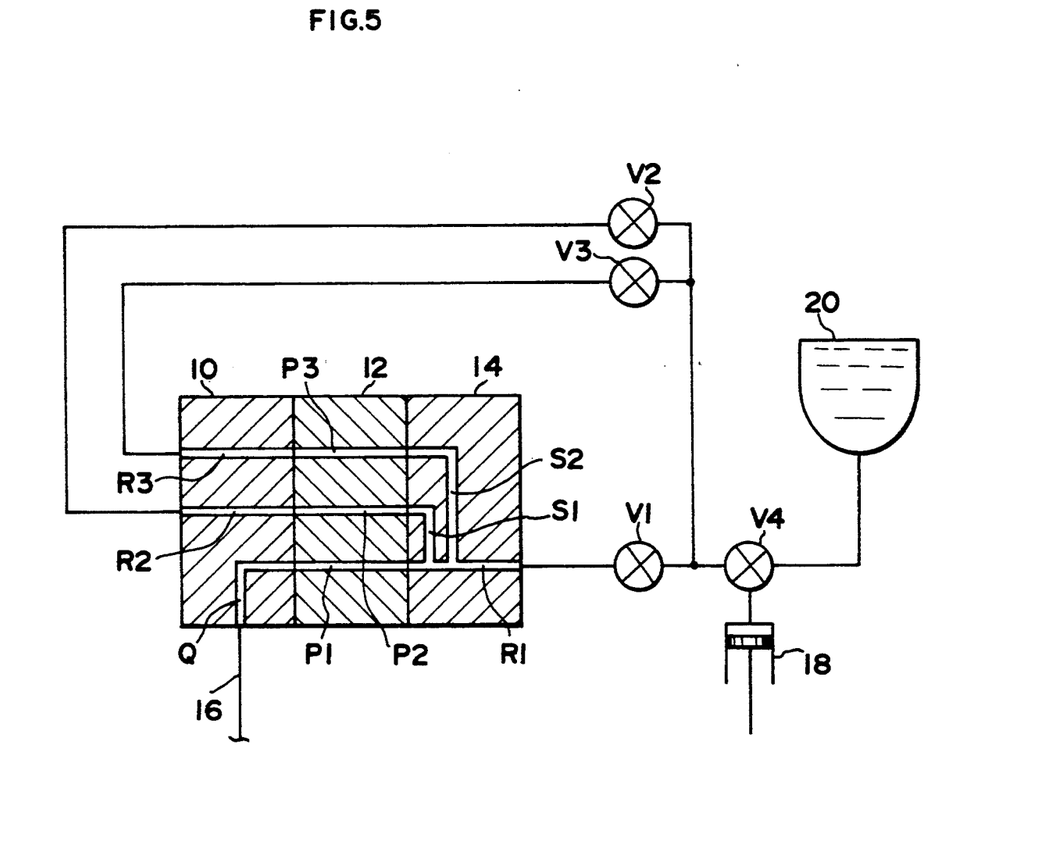
FIG. 5 is a diagram showing a different embodiment of a sampling valve of the present invention.

FIG. 5 shows a case in which three metering passages are disposed, these metering passages P1, P2, P3 are connected in series and parallel combination and parallel, and the three sampling routes are overlapped in part and parallel in part. More specifically, symbol Q denotes a flow-in passage, S1, S2 are relay passages, R1, R2, R3 are flow-out passages, and the relay passages S1, S2 are connected with the flow-out passage R1 and metering passages P2 and P3, respectively. Meanwhile, the relay passage S1 may be connected with the flow-out passage R1, and the passage S2 with passage S1.

When the valve V1 is open, and valves V2, V3 are closed, by changing over a three-way valve V4 so that aspiration means 18 and valve V1 may communicate with each other, sample flows from a pipette 16 through passages Q, P1, R1 (the first sampling route), and is measured quantitatively in the passage P1.

When the valve V2 is open, and the valves V1, V3 are closed, sample flows from the pipette 16 through passages Q, P1, S1, P2, R2 (the second sampling route), and is measured quantitatively in the passages P1, P2.

When the valve V3 is open, and the valves V1, V2 are closed, sample flows from the pipette 16 through passages Q, P1, S2, P3, R3 (the third sampling route), and is measured quantitatively in the passages P1, P3.

Figure 6:
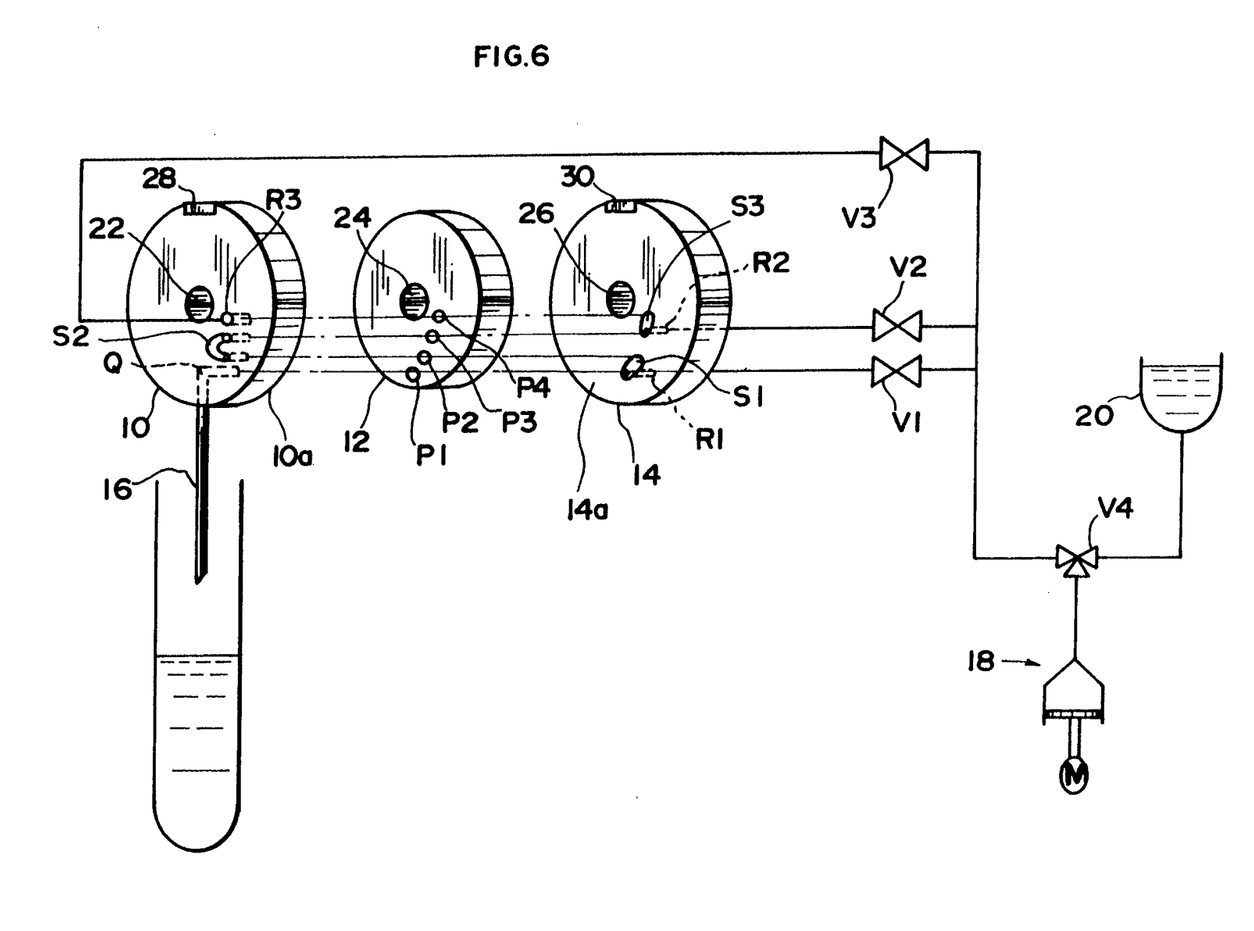
FIG. 6 is a perspective view showing a first state of filling a metering passage with sample in the sampling valve shown in FIG. 3.
Figure 7:
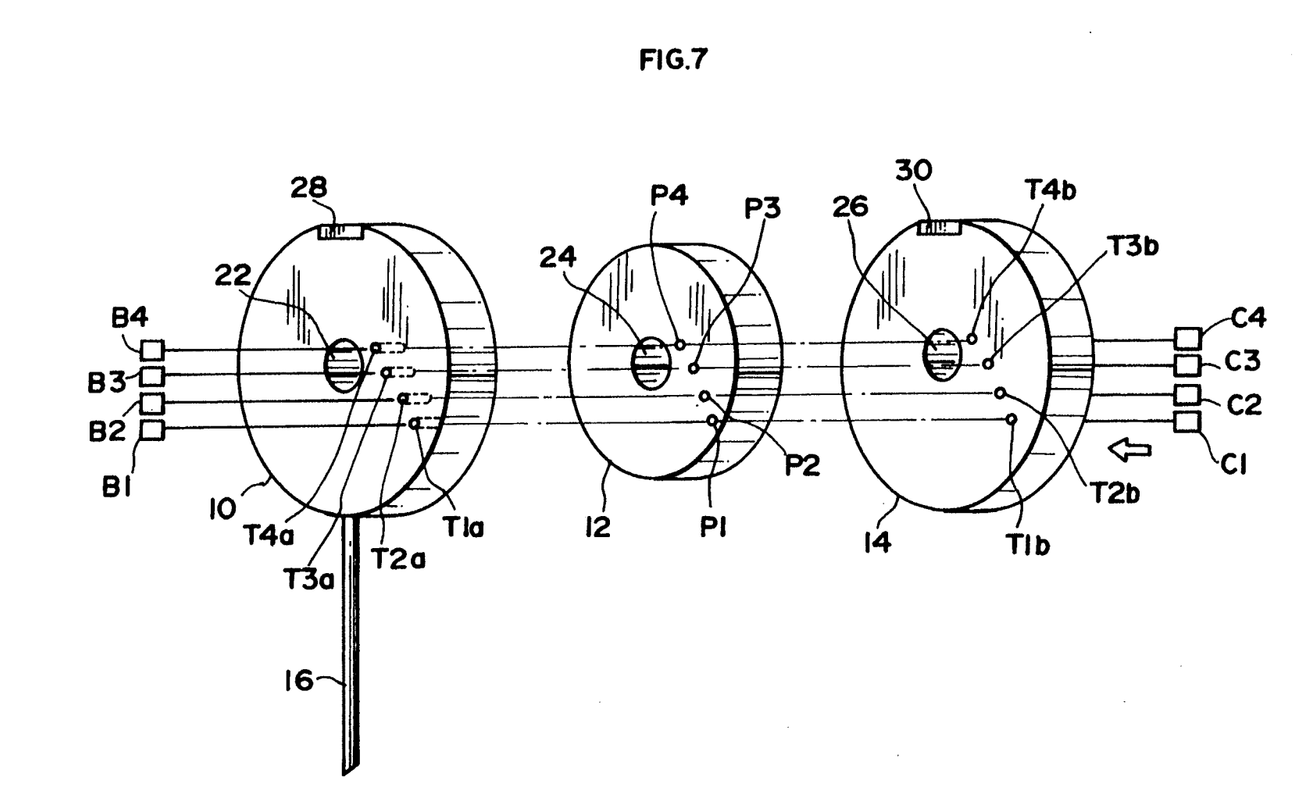
FIG. 7 is a perspective view showing a second state of pushing out and transferring the Sample in the sampling valve shown in FIG. 3.

Referring next to FIG. 6 and FIG. 7, the present invention is further described below. FIG. 6 and FIG. 7 are respective views of practical examples of the sampling valve shown in FIG. 3. FIG. 6 denotes the first state, and FIG. 7 represents the second state. In both FIG. 6 and FIG. 7, the passages are partly omitted. This is for ease of understanding of the drawing and explanation. In FIG. 6, transfer passages T1a, T1b, . . . , T4b shown in FIG. 7 are omitted (so are in FIGS. 3, 4, 5), and in FIG. 7, the passages Q, S1, S2, S3, R1, R2, R3 shown in FIG. 6 are omitted.

Referring first to FIG. 6, the sample aspiration is explained. Fixed elements 10, 14, and movable elements 12 are in disc form. In the center of elements 10, 12, 14, penetration holes 22, 24, 26 are formed, and a shaft (not shown) is passed in the penetration holes 22, 24, 26. At the upper side of the fixed elements 10, 14, notches 28, 30 are provided, in which a support (not shown) for fixing the elements is fitted. The movable element 12 is held between the fixed elements 10, 14 and rotates through a specific angle. The means for keeping the fixed elements 10, 14 in the static state and moving the movable element by a specific extent while contacting with the surface of the both fixed elements is known (for example, Japanese Laid-open Patent Hei. 1-138421). The mutually contacting surfaces of the elements 10, 12, 14 are planes polished to an extremely high precision.

The movable element 12 is, for example, provided with four passages P1, P2, P3, P4 for determining (measuring quantitatively) the sample. The metering passages P1, P2, P3, P4 are passages penetrating through the movable element 12.

At the lower side of the fixed element 10, a pipe-shaped pipette 16 is attached. The pipette 16 communicates with a flow-in passage Q in an L-shaped opening at the polished surface 10a side of the fixed element 10. Instead of the pipette 16, a fine pipe like a syringe needle may be connected through a tube to form a sample aspiration part. The passage Q communicates with the metering passage P1. On the polished surface 14a of the fixed element 14, groove-shaped relay passages S1, S3 are provided, and a loop-shaped relay passage S2 is formed outside of the fixed element 10. The relay passage S1 connects the metering passages P1 and P2, the relay passage S2 connects the metering passages P2 and P3, and the relay passage S3 connects the metering passages P3 and P4. That is, the relay passages S1, S2, S3 connect plural metering passages in series. In the portions of the relay passages S1, S3, flow-out passages R1, R2, penetrating through the fixed element 14 are provided. In the fixed element 10, a flow-out passage R3 connected to the metering passage P4 is provided. The flow-out passage R3 is also the passage which penetrates through the fixed element 10.

Numeral 18 is an aspiration means, which is, for example, a syringe type capable of generating an aspiration pressure and discharging a cleaning liquid. Numeral 20 is a cleaning liquid (diluent liquid) tank filled with liquid for cleaning (dilution) inside. A three-way valve V4 changes over the aspiration means 18 between the sampling valve side and the cleaning liquid tank side. Two-way valves V1, V2, V3 are disposed between the syringe 18 and flow-out passages R1, R2, R3, and select the route. The cleaning liquid is also used as a diluent liquid.

Thus, in the sampling valve, three sampling routes are formed, that is, the first sampling route having the flow-in passage Q as the inlet and flow-out passage R1 as the outlet, the second sampling route having the flow-in passage Q as the inlet and the flow-out passage R2 as the outlet, and the third sampling route having the flow-in passage Q as the inlet and the flow-out passage R3 as the outlet. By opening any one of the valves V1, V2, V3, and closing the others, one of the three sampling routes may be selected.

Next is explained the sample transfer by reference to FIG. 7. From the first state in FIG. 6, the movable element 12 rotates by a specific angle to become the second state in FIG. 7. In the fixed element 10, transfer passages T1a, T2a, T3a, T4a penetrating through the fixed element 10 are provided so as to communicate with the metering passages P1, P2, P3, P4, respectively. Also in the fixed element 14, transfer passages T1b, T2b, T3b, T4b penetrating through the fixed element 14 are provided to similarly communicate with the metering passages P1, P2, P3, P4, similarly. As the diluent liquid discharge means C1, C2, C3, C4 are put in action, a specific volume of diluent liquid is supplied in the direction of the arrow from the transfer passages T1b, T2b, T3b, T4b of the one side, and the sample determined (measured) quantitatively in the passages P1, P2, P3, P4 is transferred from the passages T1a, T2a, T3a, T4a into the measuring parts B1, B2, B3, B4 together with the diluent liquid. At this time, the diluent liquid discharge means operates depending on the selected sampling route. That is, when the first sampling route is selected (the sample is determined quantitatively in the passage P1 only), only the diluent liquid discharge means C1 is put in action. When the second sampling route is selected (the sample is determined quantitatively in the passages P1, P2, P3), the diluent liquid discharge means C1, C2, C3 are put in action. When the third sampling route is selected (the sample is determined quantitatively in the passages P1, P2, P3, P4), all diluent liquid discharge means C1, C2, C3, C4 are put in action.

Cleaning of the passages is explained next by referring to FIG. 6. From the second state in FIG. 7, the movable element 12 reversely rotates by a specific angle to return to the first state in FIG. 6. In the case of cleaning, too, considering same as in the case of transfer described above, the passages are cleaned according to the selected sampling route. That is, when the first sampling route is selected (sample remains in the passages Q, R1), only the valve V1 is opened and the aspiration means 18 is put in action. In this way, the aspiration means 18 exhibits the functions of both an aspiration and cleaning means. When the second sampling route is selected (sample remains in the passages Q, S1, S2, R2), only the valve V2 is opened. When the third sampling route is selected (sample remains in the passages Q, S1, S2, S3, R3), only the valve V3 is opened. In such manner, however, cleaning of passage S1 is insufficient in the first sampling route, cleaning of passages R1, S3 is insufficient in the second sampling route, and cleaning of passages R1, R2 is insufficient in the third sampling route, and therefore, when the first sampling route is selected, it is desired to open the valve V2 as well as the valve V1, and when the second sampling route or third sampling route is selected, it is desired to open the valves V1, V2, V3. Besides, when the valves V1, V2, V3 are manipulated in consideration of the sample remaining in each passage, cleaning may be done more effectively within a specified time, and at specified flow rates. For example, when the first sampling route is selected, the valves V1, V2 are opened and closed alternately repeatedly (however, the opening time of the valve V1 should be set longer). When the second sampling route or third sampling route is selected, the valves V1, V2, V3 are alternately opened and closed repeatedly (however, the opening time of the valve V2 should be set longer than that of the valves V1, V3 in the case of second sampling route, and the opening time of the valve V3 should be set longer than that of the valves V1, V2 in the case of third sampling route). As the practical cleaning method, other various manners may be considered and may be properly selected depending on the actual configuration of the apparatus.

Being thus constructed, the present invention brings about the following effects.

(1) Plural flow-out passages are provided, and each passage in the sampling valve is connected in a desired state, and therefore plural sampling routes may be formed in the sampling valve, so that only a necessary sample may be selected and taken quantitatively without any waste of sample.

(2) Since only the necessary sample is selected and taken quantitatively, only the necessary portion is sampled for each specimen and is analyzed, that is, it is possible to be applied to a so-called discrete test.

Having described preferred embodiments of the present invention with reference to the accompanying drawings, it is to be understood that the present invention is not limited to those precise embodiments, and that various changes and modifications may be effected therein by one skilled in the art without departing from the scope or spirit of the present invention as defined in the appended claims.

What is claimed is:

1. A valve for a liquid specimen, sampling comprising: two fixed elements; and a movable element held between and movable relative to said fixed elements, said movable element having plural sample metering passages disposed therein, said movable element moving while contacting a surface of each of said fixed elements so as to define a first state for filling the metering passages with sample and a second state for pushing out said sample and transferring it outside of the sampling valve, wherein:

a flow-in passage is disposed in one of said fixed elements for communicating with at least one metering passage in said first state, plural flow-out passages are disposed in either fixed element so as to fluidly communicate with mutually different metering passages in said first state, relay passages are disposed in either fixed element for mutually connecting the metering passages in specified combination in said first state, and at least one relay passage is connected with any one of the flow-in passages, flow-out passages, and other relay passage to form plural sampling routes in the sampling valve, thereby sampling the specimen by selecting a specific metering passage.

2. A sampling valve of claim 1, wherein said relay passages are provided for connecting said plural metering passages in series.

3. A sampling valve of claim 1, wherein said relay passages are provided for connecting said plural metering passages in parallel.

4. A sampling valve of claim 1, wherein said relay passages are provided for connecting said plural metering passages in series and parallel combinations.

* * * * *